United States Patent [19]

Young

[11] Patent Number: 5,749,877
[45] Date of Patent: May 12, 1998

[54] TOOL BIT FOR USE IN ULTRASONIC REMOVAL OF PLASTICS EMBEDMENT OF AN OSTEAL PROSTHESIS

[75] Inventor: Michael John Radley Young, Ashburton, United Kingdom

[73] Assignee: Orthosonics Ltd., Ashburton, United Kingdom

[21] Appl. No.: 422,989

[22] Filed: Apr. 17, 1995

Related U.S. Application Data

[62] Division of Ser. No. 216,805, Mar. 23, 1994, Pat. No. 5,536,272.

[30] Foreign Application Priority Data

Mar. 26, 1993 [GB] United Kingdom ............ 9306380

[51] Int. Cl.⁶ .................................. A61B 17/56
[52] U.S. Cl. .................. 606/99; 606/86; 606/87; 128/898
[58] Field of Search ............... 606/86, 99, 87; 128/898

[56] References Cited

U.S. PATENT DOCUMENTS

| | | | |
|---|---|---|---|
| 4,248,232 | 2/1981 | Engelbrecht et al. | 128/305 |
| 5,019,083 | 5/1991 | Klapper et al. | 606/86 |
| 5,151,099 | 9/1992 | Young et al. | 606/27 |
| 5,167,619 | 12/1992 | Wuchinich | 604/22 |
| 5,324,297 | 6/1994 | Hood et al. | 606/99 |
| 5,330,481 | 7/1994 | Hood et al. | 606/86 |

*Primary Examiner*—Michael Buiz
*Assistant Examiner*—Daphna Shai
*Attorney, Agent, or Firm*—Hopgood, Calimafde, Kalil & Judlowe

[57] ABSTRACT

An elongate tool bit is disclosed for ultrasonic excitation to remove plastics cement around a prosthetic implant in bone, as in a hip-joint replacement procedure. The tool bit features a stem portion with a distal-end claw formation, in the nature of a proximally open cup, having a convexly rounded distal end, with longitudinal apertures that provide through-passage for proximally directed flow of melted plastic. When the claw formation is driven via longitudinal vibration of the stem, cement melts at and near the convex distal end of the claw formation, and melted plastic passes through the apertures in the proximal direction to accumulate within and proximally of the claw formation. The claw formation features a relatively sharp proximally facing lip, thereby permitting the distal end of the tool to additionally serve an ultrasonic scraper function against the imbedded outer surface of the stud part of an appliance which requires replacement; alternatively, the tool can be used to ultrasonically remove plastics cement from the embedment of a distal fragment of a prosthetic appliance which has been broken, thereby aiding a procedure to remove the embedded fragment.

5 Claims, 6 Drawing Sheets

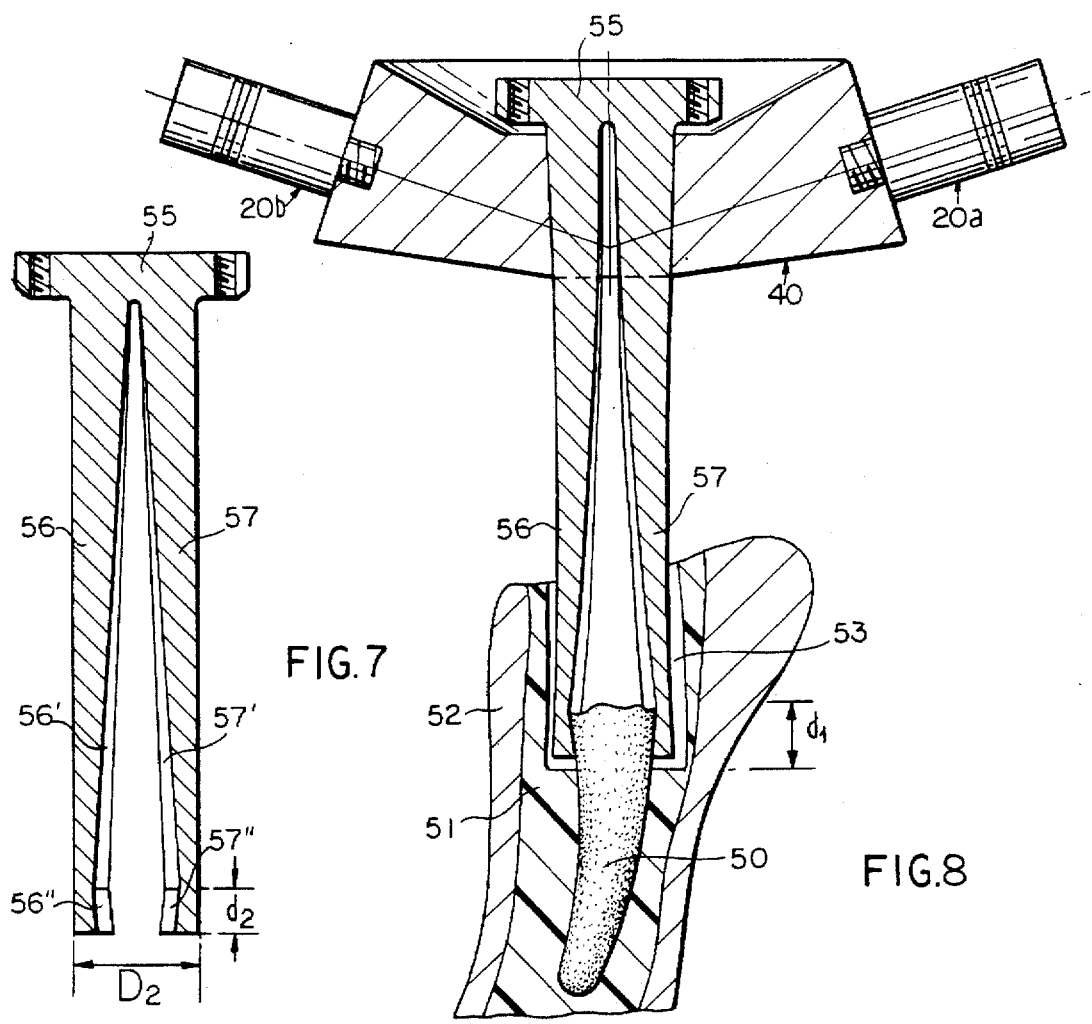

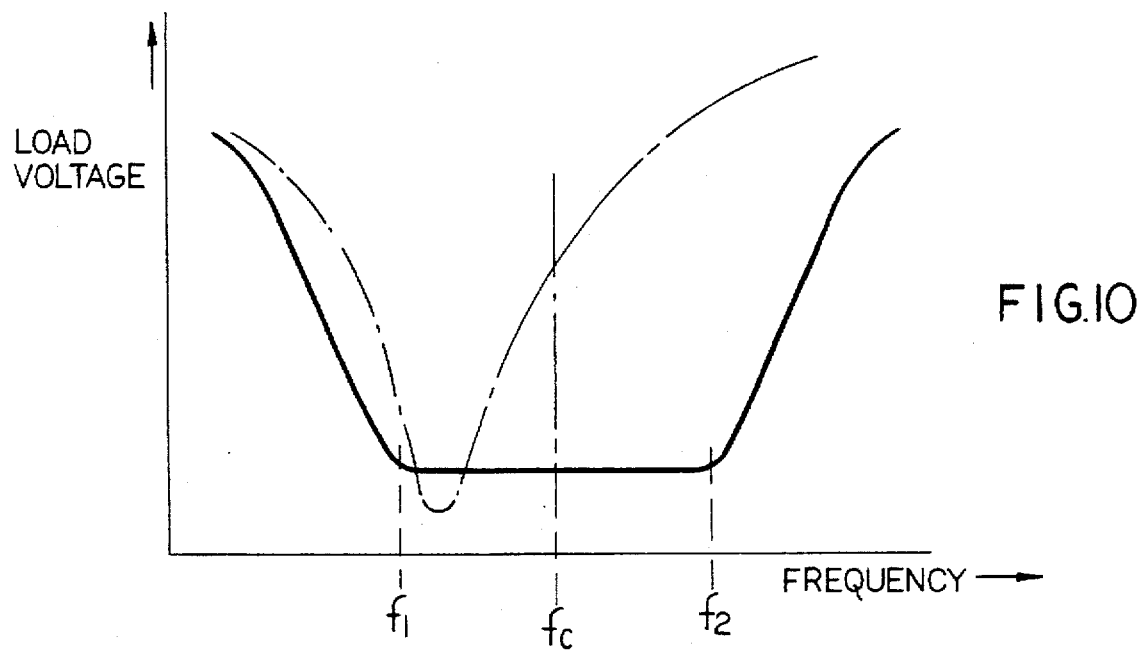
FIG.10
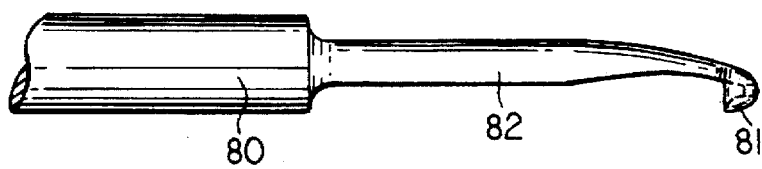
FIG.12
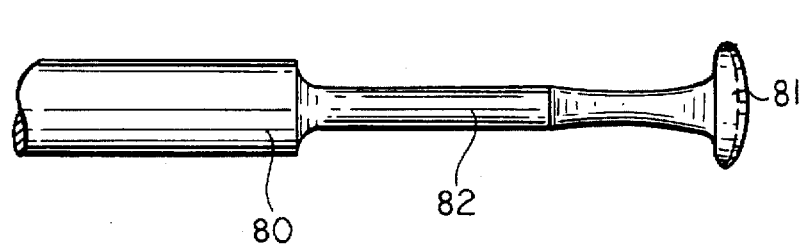 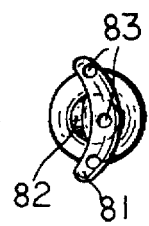
FIG.11  FIG.13

TOOL BIT FOR USE IN ULTRASONIC REMOVAL OF PLASTICS EMBEDMENT OF AN OSTEAL PROSTHESIS

RELATED CASES

This is a division of application Ser. No. 08/216,805 filed Mar. 23, 1994, now U.S. Pat. No. 5,536,272.

BACKGROUND OF THE INVENTION

The invention relates to an ultrasonic method and means for removing an osteal prosthesis from cemented installation in a living bone, as in the course of revision arthroplasty.

It is known from U.S. Pat. Nos. 4,248,232 and 5,151,099 that ultrasound may be used to facilitate removal of bone cement (PMMA) during revision arthroplasty. Local heating, by preferential absorption of ultrasound energy, raises the temperature of a small volume of the cement above the glass-transition temperature, thus allowing the cement to flow and to be manipulated into a shape and form which may be readily removed from the revision site.

It has also been claimed (Hood, et al., U.S. Pat. No. 5,045,054) that the application of ultrasound directly to the prosthesis can break the bond between the prosthesis and surrounding cement or, in the case of uncemented prostheses, between the prosthesis and in-grown cancellous bone. The direction of applied ultrasonic energy is in line with the central axis of an implanted prosthetic device, such as the axis of stem support for the ball of a hip-joint replacement. But the in-line application of force, as in the context of the Hood, et al. system, is to require the patient to oppose the force, with inevitable trauma for the patient.

BRIEF STATEMENT OF THE INVENTION

It is an object of the invention to provide an improved method and means for dislodging an installed osteal prosthesis with a minimum of trauma for the patient who is faced with the need of revision arthroplasty.

A specific object is to meet the above object for the case of revision arthroplasty of a hip-joint prosthesis that has been implanted and cemented in a femur.

It is a general object to meet the above objects with a method and apparatus of reliably high performance without a daunting level of operating complexity, which method and apparatus are applicable to the full variety of currently available prostheses.

The invention in its preferred embodiment meets these objects in an ultrasonically driven technique wherein an annular body of relatively great mass is solidly chucked around the exposed proximal end of a hip-joint prosthesis which has been cemented in the medullary canal of a femur. In most cases, the exposed proximal end is a sphere or ball at the projecting end of a stem, all integrally formed with the implanted remainder of the prosthetic device. The annular body is excited into ultrasonic radial-mode oscillation by a driver having a directional axis of mechanical oscillation, wherein the said axis is preferably radially inward through body material, toward the body axis, and preferably for substantial alignment with the center of the exposed ball or head end of the prosthesis to be removed, as for prosthetic replacement in the patient. In response to such excitation, the annular body reacts with radial-mode resonant oscillation, involving circumferentially continuous application of radially modulated squeezing transfer of ultrasonic energy into the prosthetic at the region of chucked engagement; and, in turn, the prosthetic responds to the radial-mode resonance by such plastic-deformation of its cemented and/or bony-ingrowth attachment to the patient's limb, as to locally generate enough heat to melt cementing plastic at interface with the prosthetic, or to mechanically sever bony ingrowth at interface with the prosthetic. The ultrasonically driven body annulus is of such design as to selectively accommodate a variety of sizes of prosthetic-head chucked engagement, as by selected use of one out of a group of chucks, each of which is configured for clamping a different size or shape of prosthetic head. The body annulus will also accommodate a special tool which lends itself to coupling to the buried end of a broken fragment of a prosthetic shaft, with an ability to transfer sufficient ultrasonic energy through the tool and into the broken and buried prosthetic fragment, for clean and efficient dislodging and extraction of the buried fragment.

BRIEF DESCRIPTION OF THE DRAWINGS

In the drawings which show various illustrative embodiments of the invention:

FIG. 7 is a view in longitudinal section of a tool element usable in conjunction with any of the devices of FIGS. 1, 2, 3, 5 or 6, for removal of a distal broken end of prosthetic device;

FIG. 8 is a sectional view to show use of the tool of FIG. 7 in the device of FIG. 6;

FIG. 10 is a graph to illustrate a frequency band characteristic of ultrasonic operation, using circuitry of FIG. 9;

FIGS. 11 and 12 are front and side elevation of a tool element for removing small quantities of cement; and FIG. 13 is an end view of the tool element of FIGS. 11 and 12.

DETAILED DESCRIPTION

Figure 1:
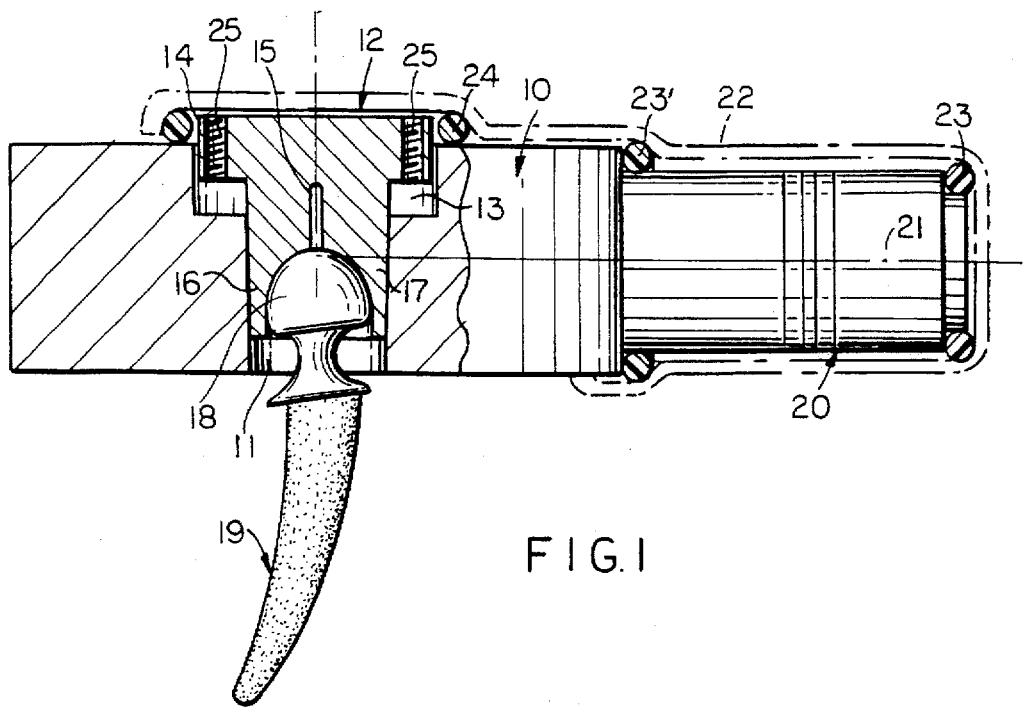
FIG. 1 is a view in side elevation, partly broken-away and in section, to show elements of a prosthetic-removal device of the invention.

Referring initially to FIG. 1, the invention is shown in application to a radial-mode oscillator comprising an annular body 10 of relatively great mass, suitably of stainless steel. Body 10 is of generally right-cylindrical configuration and has a central bore 11 which is slightly convergent in the downward direction, for the purpose of coaction with a chuck or collet member 12. At its upper end, bore 11 expands via a counterbore 13 which will accommodate the radially flanged head end 14 of member 12. The chuck or collet member 12 has a reduced distally extending lower end which is longitudinally split, as at slit 15, to define plural distal fingers, here shown as the two fingers 16, 17, in view of the single slit 15.

In the case of FIG. 1, the exposed spherical head or ball 18 of an installed hip prosthesis 19 is securely engaged by concave spherical formations within the distal or finger end of member 12, i.e., within confronting internal concave spherical surfaces of the two fingers 16, 17, it being understood that the concavities of fingers 16, 17 cooperatively define a hemispherical socket against which a ball head 18 intimately nests. The external surfaces of fingers 16, 17 preferably conform to convergence of the body bore 11 such that, once the ball head 18 has been inserted into the unstressed socket defined by the internal concave spherical surfaces of fingers 16, 17, the collet or chuck member 12 may be driven downward to securely and circumferentially continuously engage and grip the ball head 18. The drive to establish such a grip can be obtained by hammer blows delivered axially to the flanged upper end 14; in the course of such a drive, fingers 16, 17 are inwardly deflected by wedge action between the convergent concave and convex tapering surfaces, and it will be understood that in a finally chucked position, as in FIG. 1, the ball head 18 not only has virtually equatorial grip by the fingers 16, 17, but that this grip is also similarly circumferential for axially extending areas above and below the equatorial location. Alternatively, the surgeon may be of the view of hammer blows might result in trauma to the patient, in which case a pair of opposed C-clamps applied to squeeze the flange of member 12 with respect to the lower annular surface of body 10 is indicated, for a reduced likelihood of trauma.

To excite the described body 10 and its securely chucked prosthetic device 19, an electromechanical transducer 20 is shown secured locally to the periphery of body 10. Transducer 20 is suitably of the piezoelectric ceramic variety generally as shown and described (at reference number 1) in U.S. Pat. No. 5,151,099 and in pending application Ser. No. 08/199,112, filed Feb. 22, 1994, now abandoned, to which reference is made for greater detail. Transducer 20 is cylindrical and has a central axis 21 of mechanically resonant oscillation, at a frequency in the range 20 kHz to 40 kHz. The transducer is driven as the electrical load of circuitry to be described later in connection with FIG. 9, but which will be indicated here to feature a phase-locked loop for automatic high-Q tuning over a range of frequencies. The range of frequency adjustment will be understood to be that which best serves the mechanically resonant properties of body 10 and its well chucked connection to prosthetic 19, and the latter will be further understood to be in its embedded condition, and to have been the subject of an arthroscopic femoral procedure which now requires replacement.

To give an indication of size, a radial-mode resonant body 10 to accommodate a ball head 18 of 1-inch diameter is suitably of 5 to 6 inches diameter, with an axial thickness of two inches; and transducer 20 may suitably be of 3.0 to 3.5-inches overall length and 1.0 to 1.6 inches diameter.

A housing recommended for the described parts may generally be as shown and described in pending patent application Ser. No. 08/199,112, as long as the housing enables safe handling during ultrasonic operation. The phantom outline 22, with elastomeric O-ring supports at 23, 23', 24 will be understood to be suggestive of such a housing. The housing 22 happens to be removable, cylindrically surrounding the transducer 20 and thus providing a handle that is mechanically insulated from transducer resonance, and with an upper looping ring portion removably centered on and surrounding the flanged upper end of the chuck or collet member 12.

In operation, excitation of transducer 20 induces radial-mode resonance in body 10 and in the chuck and ball-head elements securely bound within body 10. The ball-head is thus induced to track the excursions of this mechanical resonance and to couple them into the volume of the prosthetic 19, with resultant complex mechanical oscillation (featuring multiple nodes and anti-nodes) at interface between the shank of the prosthetic and such plastic cement or other bond (such as bony ingrowth) that may exist. The result is rapidly, within seconds, to melt cement and to shear bony ingrowth and thus to enable manual retraction of the radial-mode system and the prosthetic 19. In the course of such retraction, which can be relatively quickly accomplished (in view of the tapered nature of the embedded prosthetic stem), it is optional whether or not the transducer remains excited, because the embedment bond to the patient will have been severed.

A note should be made to the effect that the prosthetic appliance 19 shown for illustration herein is an integrally formed single piece, so that a dislodgement is of the entire appliance. There are, however, other appliance structures in use for the same kind of hip-joint replacement. For example, the ball head 18 may have been a separately manufactured ball having a radial bore for "permanent" Morse-taper fit to an otherwise exposed stud which is an integral part of the prosthetic. In that event, the described ultrasonic radial-mode excitation of the exposed ball of the prosthetic appliance may result in dislodging the ball from its Morse-taper fit, thus exposing the tapered stud portion of an appliance that remains embedded in the patient. For such a situation, it will be understood that a second radial-mode system as described for FIG. 1 may be at hand and equipped with a chuck or collet having internal concave contours suited for axially extensive and for virtually circumferentially continuous engagement with the otherwise exposed stud end of the prosthetic. Ultrasonic excitation of the chucked stud will then achieve the same desired result of inducing such mechanical action at the embedded interface or interfaces within the body as to enable quick and efficient retraction of the prosthetic.

Once the prosthetic has been removed, personnel aiding the surgeon can address the problem of disengaging the chuck and the chucked prosthetic from the radial-mode body. To this end, angularly spaced plural tapped bores 25 in the flanged end of the chuck may be threaded with bolts (not shown), for axially jacking reference to the flat inner annular end of the counterbore 13. Upon a sufficiently jacked displacement, the chuck action becomes dislodged and the prosthetic and the chuck 12 may be removed from each other and from body 10.

Figure 2:
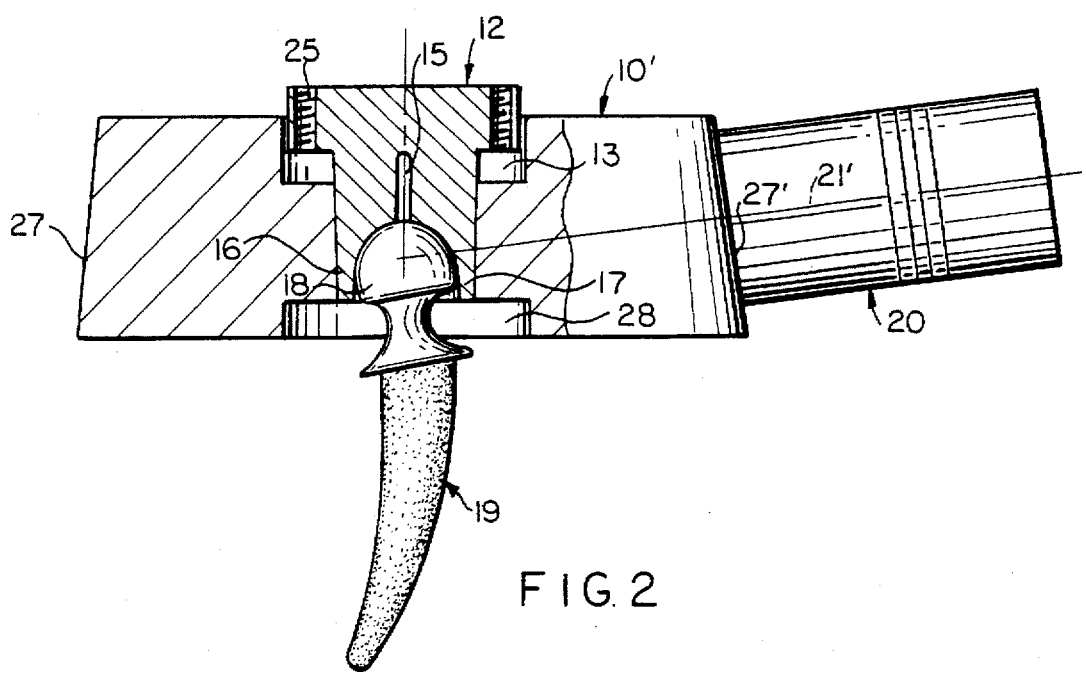
FIG. 2 is a view similar to FIG. 1 to show a modification.

The embodiment of FIG. 2 represents slight modification from what has been described for FIG. 1, and the same reference numbers are re-used where possible. The chief difference in FIG. 2 is that the directional axis 21' of ultrasonic excitation by transducer 20 is not only oriented radially inward, but axis 21' is also inclined downwardly for intersection at or near the spherical center of the concave spherical inner surfaces of fingers 16, 17, thus at or near the spherical center of a ball or ball head 18 chucked thereto. To this end, the annular body 10' for excitation into radial-mode mechanical oscillation has an outer surface 27 which is frusto-conical so that the inclined driving end face of transducer 20 may be mounted to a locally milled flat 27' in the frusto-conical outer surface. Further, FIG. 2 shows an additional counterbore 28 at the lower end of the central bore of body 10' to provide greater concentration of ultrasonic energy from body (10') structure to an exposed ball head and associated bone structure (not shown in FIG. 2). Action and use are otherwise as indicated for the structure of FIG. 1.

Figure 4:
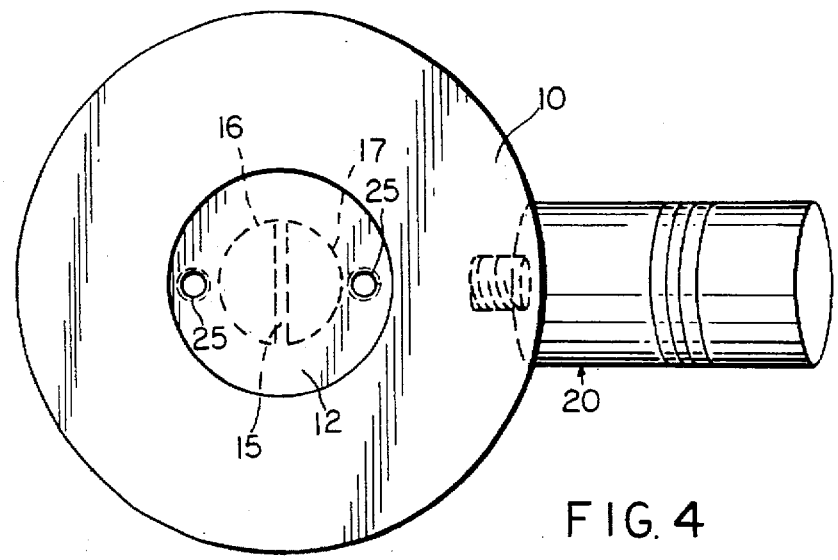
FIG. 4 is a plan view of the device of FIG. 3.
Figure 3:
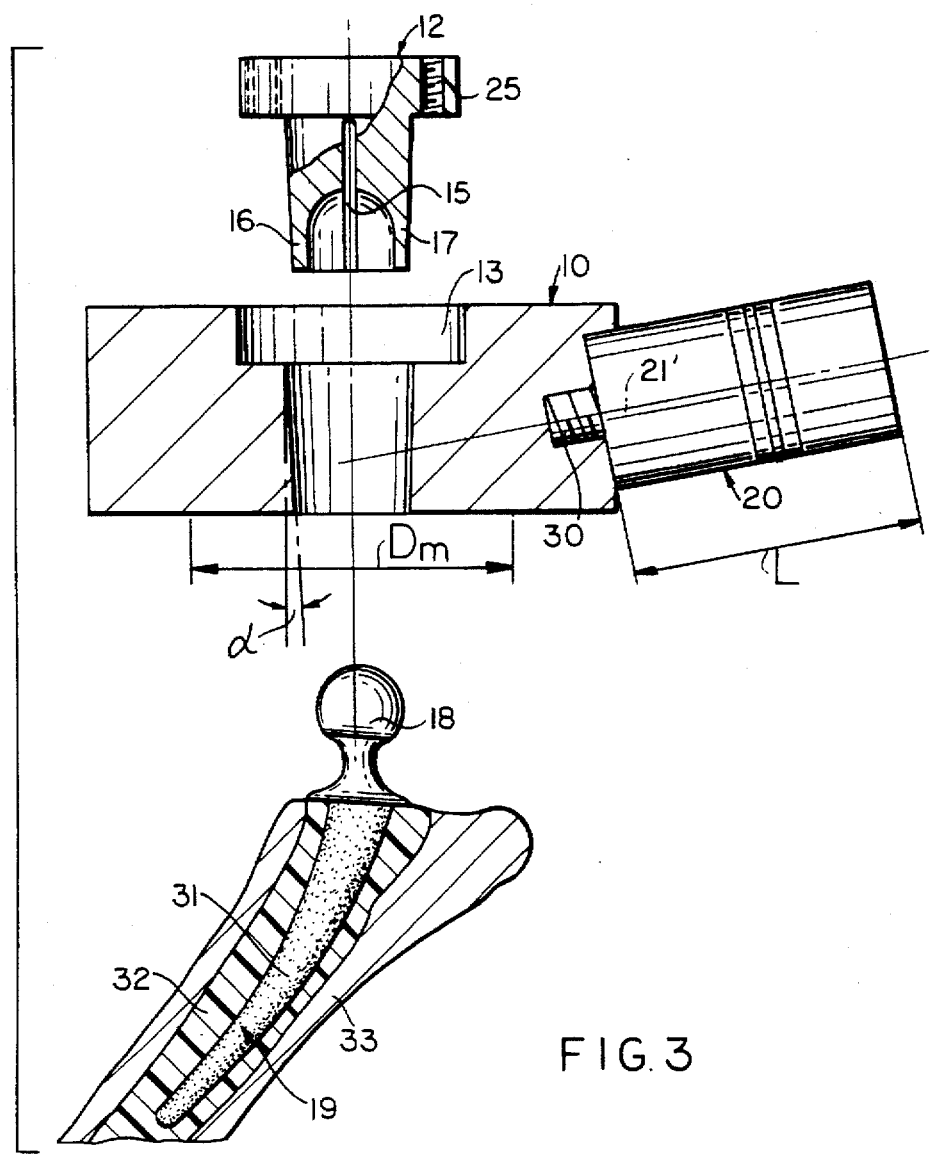
FIG. 3 is an exploded view of separable parts, as in FIG. 2.

FIGS. 3 and 4 depict in greater detail an alternative version of the modification of FIG. 2, wherein the axial direction 21' of ultrasonic excitation from transducer 20 into body 10 is again radially inward and also downwardly tilted for anticipated near-center delivery to the spherical center of a chucked ball head 18. In FIG. 3, body 10 is again cylindrically annular as in FIG. 1, and the driving end of transducer 20 is received in a shallow, suitably inclined local bore in the periphery of body 10, for flat-to-flat end-face delivery of mechanical oscillation to body 10; in FIG. 3, a reduced stud portion 30 of the driving end face of the transducer is shown in tightly threaded engagement with a tapped bore at the base of the transducer-seating bore in body 10.

The greater detail of FIG. 3 enables identification of further features common to all embodiments of the present invention. The threaded mounting via a stud is at 30, with otherwise flat-to-flat end interface from the transducer to the radial-mode body; such a flat-to-flat interface can be taken as presently preferred for all embodiments. The length L of the transducer should be an integer number of half-wavelengths of sound transmission in the medium of the transducer; this medium is suitably a conventional sandwich of aluminum alloy and stainless steel plate elements, except of course for the piezo-electric ceramic disc and its wafer-thin electrodes which are at outward offset from the central transverse plane of the transducer. The mean diameter $D_m$ of the radial-mode body 10 is preferably such as to account for a mean geometrically circumferential extent (i.e., at diameter $D_m$) which is approximately an integer multiple of said wavelength.[1] And the slightly convergent taper angle α within the bore of body 10 is preferably in the range 10° to 20°. Anticipating substantial spherical concave-to-convex surface light engagement of the chuck or collet fingers 16, 17 to the ball or ball head 18, the concave spherical surfaces of fingers 16, 17 are preferably generated when fingers 16, 17 are radially inwardly displaced to the extent of an ultimately chucked state; and the outer-surface contouring of the chuck fingers 16, 17 is such as to develop progressive inwardly cantilevered bending to lock onto a ball or ball head 18 in the course of hammering or other axially jacked displacement into the fully chucked position shown for all embodiments except for the exploded diagram of FIG. 3.

[1] This whole-wavelength criterion for radial-mode resonance in a different context appears in the paper, "The deign of high-intensity radial vibrators for metal working applications", Young, et al., J. Phys. D: Appl. Phys., 1971, Vol. 4, pages 212 to 214.

Finally, FIG. 3 illustrates the environment for use of a radial-mode system for all embodiments of the invention, namely, that the tapered stem portion 31 of the involved prosthetic device 19 has the environment of plastic cement 32, securing the prosthetic to and within an intramedullary cavity in a suitably cored and otherwise prepared proximal end of a femur 33. The relatively massive use of plastic cement 32 will be understood in FIG. 3 to have been exaggerated, and it will be understood that very often in the preparation of a femur to receive a hip-joint prosthetic 19, the stem 31 will have been installed at least in part in such direct adjacency to bone tissue as to have involved bony-ingrowth into the prosthetic; still further, the installation of prosthetic 19 may have been so installed in the femur as to have relied solely on bony ingrowth for fixation, in which case, radial-mode excitation of the body 10 will sever the bony ingrowth to permit removal of the prosthetic.

Figure 5:
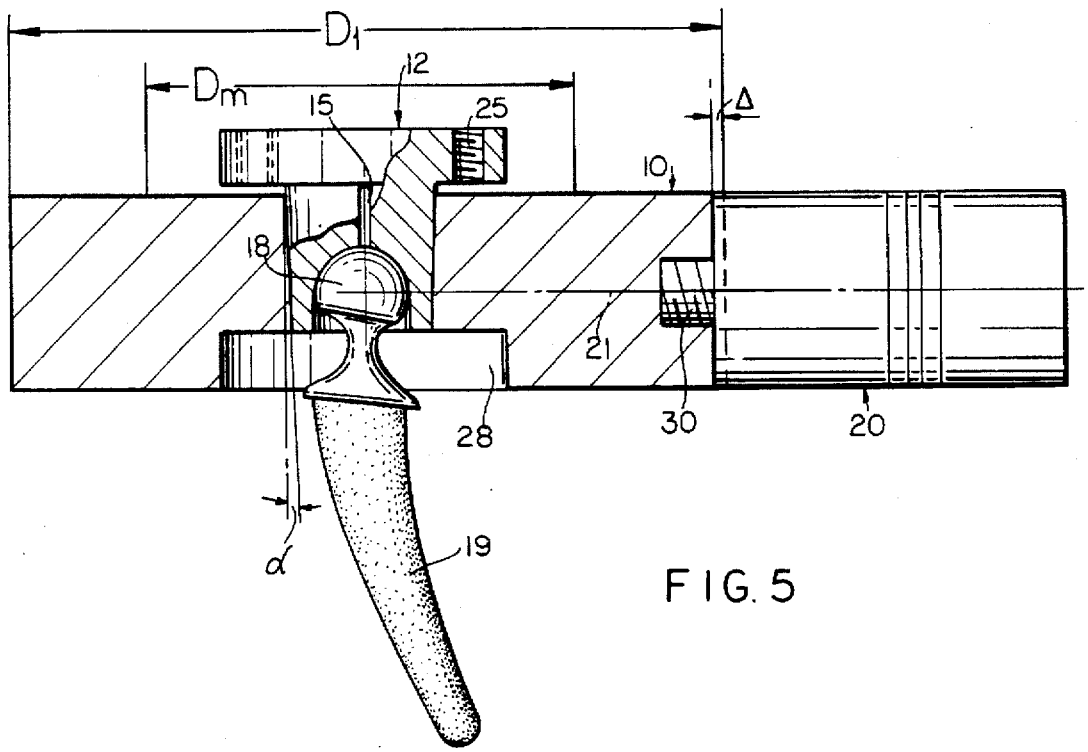
FIG. 5 is a view similar to FIG. 1 to show another modification.

In the embodiment of FIG. 5, the radial-mode body 10 is right-cylindrical and of axial thickness matching the diameter of the transducer 20. There is no counterbore into which the flanged head of chuck 12 may be accommodated (as at 13 in FIGS. 1, 2 and 3), but there is a lower counterbore 28 which enables clearance for chucked clamping of a prosthetic ball or ball head 18 with its spherical center substantially on the strictly radial transducer axis 21 of ultrasonic mechanical oscillation. Dimensioning applied to FIG. 5 identifies the cylindrical outer diameter D of body 10 and the mean diameter $D_m$. Further dimensioning at Δ identifies the fact that the body cylinder of diameter D is locally milled to a chordal flat (of radial depth Δ) for establishing a flat interface between transducer 20 and body 10, the same being tightly secured by threaded means 30.

Figure 6:
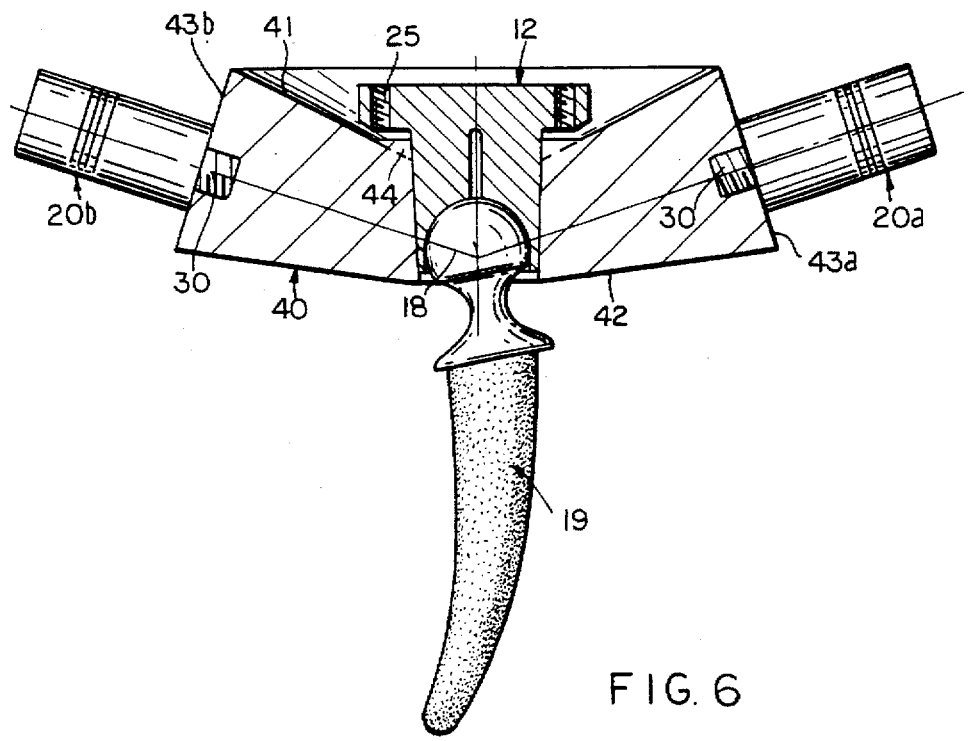
FIG. 6 is a view similar to FIG. 1 to show a further modification.

The embodiment of FIG. 6 illustrates that a radial-mode annular body 40 of the invention need not be geometrically cylindrical, and it also illustrates that plural ultrasonic transducers may be provided at angular spacing around body 40, all with their respective axes of mechanical oscillation directed to substantially the center of a ball or ball head 18 of an implanted prosthetic 19. As shown, the plurality of transducers is two, at 180° spacing about the central axis of body 40. The geometry of body 40 may be described as annular, with a central bore and chucking or collet means 12 as previously described. The annular body 40 features an upper concave frusto-conical end face 41 that is axially spaced from a lower convex frustoconical end face 42. The outer surface of body 40 is also frustoconical except for local chordal flats 43a, 43b to accept the flat-interface relation of transducers 20a, 20b at their respective connections to body 40. Preferably, the concave slope of upper surface 41 is at greater offset from a radial plane with respect to the central axis of body 40 than is the lesser such offset in the case of lower surface 42. This relationship establishes the presently preferred shape of body 40 as a dish wherein axial thickness reduces in approach to the central bore to which the chuck 12 is fitted, thus enabling radial-mode oscillation to bring resonant energy to even greater convergence at the desired locus of energy transfer to prosthetic 19. For purposes of deriving purely axial jacking force to dislodge a clamped condition of chuck 12, a small local fillet 44, one for each of the threaded jack bores 25 of the chuck flange, enables inserted jack bolts to be driven perpendicular to corresponding fillets 44.

In the removal or attempted removal of a hip-joint or other prosthetic from a patient, it sometimes happens that the stem of the prosthetic breaks or is found to have been broken, thus leaving a distally embedded fragment of the stem, as shown at 50 in FIG. 8. At the point in time illustrated by FIG. 8, it will be understood that bone cement within the proximal end of a femur 52 has been selectively removed to establish an enlarged opening 53, i.e., enlarged from the socket of bone cement left upon removal of the proximal part of the prosthetic, and it will be further understood that this enlargement has been achieved not only as far as the embedded broken piece 50 but also to the extent $d_1$ therebeyond. Bone-cement removal tooling as described in copending patent application Ser. No. 08/199,112, filed Feb. 22, 1994 is ideal for rapid and effective bone-cement removal to achieve the described enlargement, including to the predetermined depth $d_1$ beyond the location of the break which produced the embedded fragment 50.

A tool bit 80, based on the technology described in said U.S. Pat. No. 5,151,099, is shown in FIGS. 11, 12 and 13. This tool bit features a distal-end claw formation 81 which may be used to melt and extract cement in small quantities from and around the periphery of the end of the fragment 50, to provide the enlarged opening 53. The tool comprises a stem 82 wherein the claw formation 81 at its distal end is a small distally facing convexly rounded saucer-shaped or spoon-shaped cup formation having one or more longitudinal apertures 83 therethrough; when the cup at 81 is driven in longitudinal oscillation, by reason of ultrasonic longitudinal vibration of stem 82, cement melts at and near the distal side of the cup, and melted cement passes in the proximal direction through the apertures to accumulate within the cup. The tool may be withdrawn periodically to extract cement or other material and thereby to further aid formation of the enlarged opening. As shown in FIGS. 11 to 13, the mounting stem 82 has a proximal straight-axis portion 80, 82 for alignment with the longitudinal direction of ultrasonic vibration, and said mounting stem 82 is tapered with reducing section in a distal region of near-adjacency with the spoon-shaped distal end 81; said taper includes a bend in said distal-end region to place the distal end at radial offset from the longitudinal direction of said proximal straight-axis portion. In addition, when withdrawing the tool bit, its proximally facing peripheral lip may be a relatively sharp edge, permitting it to serve a scraper function in the process of forming the enlarged opening, the scraping being against the outer surface of the broken fragment 50, to enable direct grasping engagement of an extraction tool to the broken fragment.

Having thus prepared the enlargement 53 in bone cement at the proximal end of femur 52, and to the depth $d_1$ beyond the break responsible for the embedded fragment 50, all is in readiness for use of a special tool bit as shown in FIG. 7, as a replacement for the chuck or collet element 12 in any of the embodiments described in connection with FIGS. 1, 2, 3, 5, and 6 above; and in FIG. 8, the tool bit of FIG. 7 will be recognized in substitution for the chuck 12 of FIG. 6.

Briefly, the tool bit of FIG. 7 is suitably of stainless steel and comprises a flanged head 55, integrally formed with plural elongate, relatively massive but tweezer-like legs 56, 57. The outer diameter $D_2$ may be cylindrical and thus constant in manufacture of the tool bit. Within this cylindrical outer-surface profile, a gradually tapering bore establishes concave inner-surfaces 56', 57' of the legs 56, 57, all except for the distal remainder $d_2$ which is characterized by short distally convergent concave profiles 56", 57" within the distal ends of legs 56, 57. The cylindrical diameter $D_2$ is selected to permit insertional entry of the distal ends of legs 56, 57 through the upper end of the convergent central bore of the radial-mode body, the same to be inwardly cammed in the course of full insertion through this central bore. This inward camming action deflects legs 56, 57 toward each other and in all likelihood into radially loaded mutual contact of their distal ends by the time these distal ends have been extended substantially fully beyond passage through the bore of body 40. At this point it is a simple matter to compliantly spread apart the distal ends of legs 56, 57, as by inserting and twisting a screwdriver blade therebetween, the thus achieved spread being such as to permit insertion of the distal ends of legs 56, 57 into the enlarged opening 53 and past the upper end of the embedded broken fragment 50. Such insertion may be to the extent $d_2$ beyond the detection of initial contact with fragment 50, whereupon the screwdriver or other spreading device may be removed to permit legs 56, 57 to apply a compliantly stressed grasp of the proximal end of fragment 50. At this point, the grip of legs 56, 57 on the fragment 50 is sufficient for direct transfer of ultrasonic energy from the radial-mode body 40, and via the tool bit of FIG. 7, to the fragment 50, whereby to impart ultrasonic energy to the fragment for melting or breaking its interface with bone cement or with bony ingrowth, as the case may be. And of course, when thus melted or broken at this interface, the embedded fragment 50 is in readiness for immediate extraction, using the same grasp by legs 56, 57.

The various embodiments of the invention will be seen to provide a method and apparatus for the removal of osteal prostheses, when exposed or broken as a fragment that may remain buried and embedded within bone. Importantly, the method and apparatus are served by a high-mass radial-mode resonator compressionally coupled to the spherical head, or cylindrical or Morse-tapered proximal end, of the prosthesis. The system meets two principal criteria: the radial-mode resonator permits axial attachment of a rigid mass to the prosthesis, without the trauma-inducing prospect of direct ultrasonic drive of the prosthetic device distally with respect to the central axis of the ball or ball-head and its embedded stem. This result is achieved with a relatively small shift in resonant frequency, and it is compatible with the use of a fully automatic tuning system such as that which is schematically presented in FIG. 9.

Figure 9:
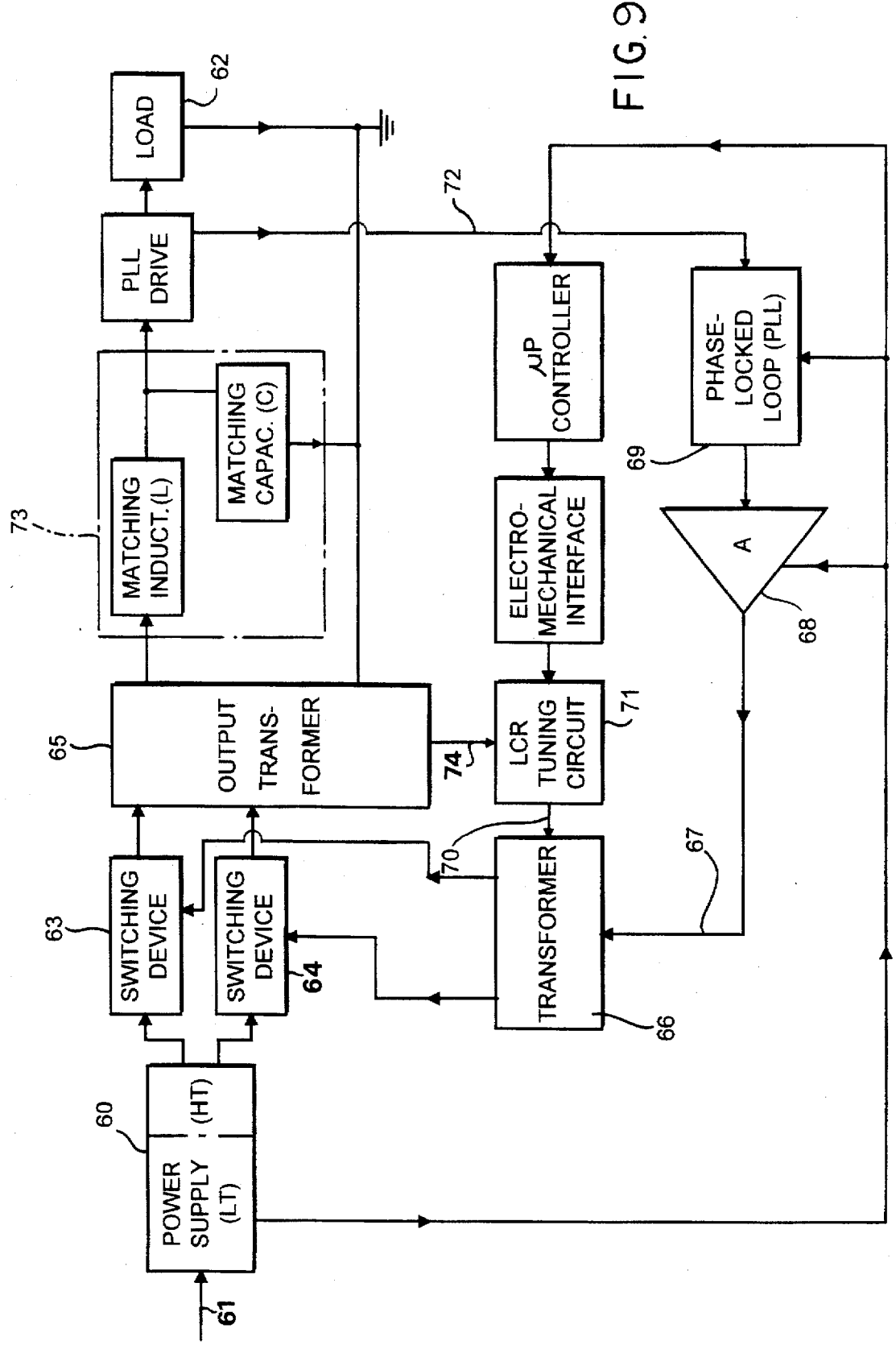
FIG. 9 is an electrical block diagram to show excitation and control circuitry for use in any of the disclosed prosthetic-removal embodiments of the invention.

FIG. 9 depicts excitation circuitry wherein phase-locked control expands the bandwidth tolerance of the system to shifts in mechanical resonance frequency, within limits, for a given setting of circuitry parameters. Specifically, a power-supply unit 60 may rely upon conventional a-c power, available at 61 as from a household wall outlet, and unit 60 derives both high-tension (HT) d-c and low-tension (LT) d-c supplies to automatic-tuning circuitry, wherein ultrasonic excitation voltage is delivered to the involved transducer 20, here symbolized as "load" 62. The HT supply is interrupted by phased high-frequency switching devices 63, 64, producing a square wave across the primary of an output transformer 66, the frequency of which is determined via a first input 67 suitably amplified at 68 from a phase-locked loop (PLL) at 69, and via a second input 70 from a microprocessor (µP) controlled LCR network 71; the LCR tuning circuit 71 is associated (via connection 74) with a low-voltage secondary winding of output transformer 65, and the tuning function of the microprocessor (µP) may be defined in software contained in an EEPROM or similar device, allowing automatic tuning over a wide frequency range. In the supply from transformer 65 to the load 63, matching values of inductance (L) and capacitance (C) are chosen to ensure sinusoidal current and voltage waveforms in the load 62 and to provide an essentially constant load-current characteristic. Feedback in line 72 reflects instantaneous output from the impedance-matching network 73 and is continuously supplied to the phase-locked loop means 69. The net result is indicated by the solid-line curve of FIG. 10, wherein phased-locked automatic tuning is seen to be ensured for the resonant-frequency band from $f_1$ to $f_2$, indicating a span of mechanical resonance that is held in tune without need for manual adjustment; for comparison, the same structure and excitation values, without the benefit of the indicated phase-locked loop and automatic tuning are to be understood as producing the essentially single-tuned frequency characteristic that is shown by the phantom-line curve of FIG. 10.

What is claimed is:

1. A tool for use in revision arthroplasty wherein a prosthetic member to be removed is at least partially encumbered by bone cement, characterized in that it comprises an elongate stem adapted for connection to ultrasonic longitudinal oscillation, said stem having a distally facing convexly rounded spoon-shaped distal end provided with one or more spaced longitudinal apertures through which said cement melted by ultrasonic vibration of said tool may pass for external removal, said tool being so dimensioned that it is adapted to remove said cement immediately adjacent said prosthetic member.

2. A tool for use in revision arthroplasty wherein a prosthetic member to be removed has an elongate distally extending mounting stem that is at least partially encumbered by bone cement, characterized in that said tool comprises an elongate tool stem adapted for proximal connection to a generator of ultrasonic longitudinal oscillation, said tool stem having a distally facing convexly rounded spoon-shaped distal end having a proximally open concave wall provided with longitudinal apertures through which the cement melted by ultrasonic vibration of said tool may pass for external removal, said tool being so dimensioned that it is adapted to remove the cement immediately adjacent said prosthetic member.

3. The tool of claim 2, in which said spoon-shaped distal end is defined by radially spaced inner and outer arcuate limits wherein the inner arcuate limit is adapted to conform generally to the local external contour of a cement-encumbered region of the mounting stem of the prosthetic member, said limits being taken in a proximal geometric plane which is substantially normal to the elongate direction of said mounting stem.

4. The tool of claim 3, in which angularly spaced end-wall formations integrally interconnect said inner and outer arcuate limits, thereby completing a peripherally continuous proximal lip contour of said spoon-shaped distal end.

5. The tool of claim 2, in which said mounting stem has a proximal straight-axis portion for alignment with the longitudinal direction of ultrasonic vibration, and said mounting stem is tapered with reducing section in a distal region of near-adjacency with said spoon-shaped distal end, said taper including a bend in said distal-end region to place said distal end at radial offset from the longitudinal direction of said proximal straight-axis portion.

* * * * *